(12) United States Patent
Allon

(10) Patent No.: US 8,371,852 B2
(45) Date of Patent: *Feb. 12, 2013

(54) IMPLANT AND A METHOD FOR USING THE SAME

(76) Inventor: Dror Michael Allon, Modi'in (IL)

(*) Notice: Subject to any disclaimer, the term of this patent is extended or adjusted under 35 U.S.C. 154(b) by 45 days.

This patent is subject to a terminal disclaimer.

(21) Appl. No.: 12/902,759

(22) Filed: Oct. 12, 2010

(65) Prior Publication Data

US 2011/0086325 A1  Apr. 14, 2011

Related U.S. Application Data

(63) Continuation-in-part of application No. 12/357,095, filed on Jan. 21, 2009, now Pat. No. 8,033,827.

(60) Provisional application No. 61/022,366, filed on Jan. 21, 2008.

(51) Int. Cl.
*A61C 8/00* (2006.01)
*A61C 13/225* (2006.01)
*A61F 2/02* (2006.01)

(52) U.S. Cl. ........................ 433/173; 433/172; 623/17.17

(58) Field of Classification Search .......... 433/172–176, 433/201.1, 80, 202.2, 215, 220, 221; 623/17.17
See application file for complete search history.

(56) References Cited

U.S. PATENT DOCUMENTS

| 4,523,910 A * | 6/1985 | Makovich ................. 433/80 |
| 4,671,768 A * | 6/1987 | Ton ........................ 433/174 |
| 5,584,688 A * | 12/1996 | Sakuma et al. ............. 433/81 |
| 5,915,967 A * | 6/1999 | Clokie ................... 433/173 |
| 5,968,098 A * | 10/1999 | Winslow ............... 623/17.11 |
| 6,394,807 B2 * | 5/2002 | Robinson ................ 433/173 |
| 7,172,594 B2 * | 2/2007 | Biscup .................. 606/86 A |
| 2003/0104339 A1 * | 6/2003 | Fromovich et al. ......... 433/215 |
| 2003/0224328 A1 * | 12/2003 | Sapian .................... 433/173 |
| 2004/0068324 A1 * | 4/2004 | Grundei ................... 623/32 |
| 2005/0192675 A1 * | 9/2005 | Robinson .............. 623/23.46 |
| 2006/0008773 A1 * | 1/2006 | Liao ..................... 433/173 |
| 2007/0160954 A1 * | 7/2007 | Steiner .................. 433/173 |
| 2008/0131840 A1 * | 6/2008 | Chen .................... 433/174 |

* cited by examiner

*Primary Examiner* — Heidi M Eide
(74) *Attorney, Agent, or Firm* — Browdy and Neimark, PLLC

(57) ABSTRACT

A dental implant for coupling an artificial tooth to a jawbone of a patient is provided. The dental implant includes an elongated body having a first end threaded bone-engaging portion for engaging the dental implant with the jawbone and a second end, and wherein the dental implant is adapted to operate as a conduit for bone grafting material by enabling introduction of the bone grafting material into a grafting space extending between said elongated body and the patient's jawbone surrounding it. Preferably, the dental implant includes a plurality of longitudinal grooves located at the external surface of the threaded bone-engaging portion of the dental implant, or includes circumferentially located openings, to allow delivery of bone grafting material into the grafting space.

4 Claims, 6 Drawing Sheets

IMPLANT AND A METHOD FOR USING THE SAME

This patent is a continuation in part of U.S. Pat. No. 8,033,827 filed Jan. 21, 2009 which claims priority to provisional application 61/022,366 filed Jan. 21, 2008.

FIELD OF THE INVENTION

The present invention relates to dental implants and in particularly to methods and dental implants using bone grafting techniques.

BACKGROUND OF THE INVENTION

Dental implants have always been a subject for study and researches. In recent years the medical world has been investing a lot of effort to improve dental implants. The straightforward implant insertion procedure cannot be implemented when the edentulous alveolar ridge bone is insufficient, either in quality or quantity, (for example, fresh extraction sites, especially of multi-rooted or ankilosed teeth, that require more resection of bone to be accomplished). Furthermore, the high complication rates accompanying those cases, due to the anatomical proximity of the alveolar nerve or the maxillary sinus, poor bone quality and incorrect three-dimensional relation to the opposite dentition or ridge, are all important parameters in treatment plan considerations. Such cases are typically defined as sub-optimal alveolar ridge for implant insertion.

Under the conditions mentioned above (and others), augmentation of the future implantation site is necessary for long-term successes. This is done mostly by Guided Bone Regeneration (hereinafter "GBR"), using autogenic or allogenic bone grafting and/or allopllastic bone-substitute grafting and a biological barrier (membrane). The membrane is used for inhibition of connective-tissue proliferation into the grafted site thus, thereby creating better conditions for osteoinduction and osteoconduction by the grafting material.

The surgical procedure for GBR is technique-sensitive, and the failure rate and complication rate are considerably higher, comparing to the "simple" implant insertion procedure. Even when done by a specialist, the GBR procedure is still a time consuming procedure and thus very expensive for the patient. The surgical part of the treatment is usually divided into two or three sessions and lasts for several months. Some cases would require even more treatments due to arising complications.

By the conventional protocol of the GBR procedure of implanting a dental implant, after local anesthesia, the surgeon exposes the edentulous alveolar crestal bone at the future implant site. Granulation tissue is removed to prepare the bone defect to be grafted. Then autogenic bone harvested from other site. In the alternative, xenograft bone/allograft bone/alloplast grafting material is prepared and applied to the defect. After designing the desired ridge contour, the graft is covered by membrane. When necessary, bone pins or screws are used to avoid migration of the bone particles or the membrane over the newly-shaped ridge. The flap has to be deliberately released by means of wide reflection, releasing cuts and periosteal scoring in order to cover the augmented alveolar crest without any tension. Failure to achieve this, results in the most common cause for the aforementioned complications (dehiscence, infection of the graft and failure to achieve the required quality and quantity of alveolar bone formation).

Basically, the major difficulty lies with covering an enlarged volume of augmented bone with the same amount of soft tissue.

A second technical difficulty is the insertion of the dental implant at the same stage, since the ridge is not solid, but rather composed of a moist powder and small particles of bone or substitute. It neither can hold nor can be arranged properly around the implant and still be covered by the membrane and the mucoperiosteal flap. Mainly due to this reason, only after four to nine months, (once the bone graft is consolidated and replacement resorption by natural host bone cells occurs to some extent) a second intervention is performed. In this stage, after local anesthesia and second exposure of the bone by flap reflection, serial drills into the newly reconstructed ridge are followed by the insertion of the dental implant. Next, the flap is sutured over the implant and an additional healing (osseointegration) period of three to six months is usually required.

After the latter healing period, a third surgical intervention is needed for the implant head exposure and the connection of a trans-mucosal part as a healing cup, which is than replaced after few weeks by a prosthetic platform for restoration of the tooth. This stage requires local anesthesia and sutures, as well. Hence a total of three surgeries and three appointments for suture removal are usually needed while carrying out the conventional procedure.

Nowadays, most dental implants are made of Titanium and are shaped as a cylinder or a screw. Bone grafting materials are commercially available in various forms and consistencies as xenografts, allografts or alloplasts delivered as block, powder, grains, putty or gel. Some of the materials require preparation or manipulation during surgery, rendering them exposed to the non-sterile environment of the dental clinic and to an increased contamination risk. Delivery of the grafted material is usually done by dental spatula or special syringe which is neither accurate nor efficient.

Polypeptide growth factors are recombinant biologic mediators that regulate cellular activity. They include growth factors (e.g. PDGF, TGF-β, igf-1, vegf and the like), differentiation factors (e.g. BMP-2, OP-1, GDF-5, GDF-7), matrix factors (such as fibronectin, vitronectin, thrombobospondin-1) and platelets-rich plasma ("PRP"). Recent studies demonstrated induction of bone growth by rhBMP-2, carried by injectable collagen or semisolid calcium-phosphate cement, in craniofacial and dentoalveolar defect in animals model and human.

Recently, commercially available rhBMP-2 (induct-os®, INFUSE®) and op-1® putty were approved for clinical use by the FDA, Some of them for maxillofacial application. Topically administered Statins also play role in activation of osteogenesis and potentiation of BMP. The above agents and others that may have been developed for the same purposes, will be referred to hereinafter as "grafting materials"

Another crucial part of the above-described procedure is the GBR membranes, which are available as sheath or mesh of absorbable (collagen) or non-absorbable material (such as PTFE or Titanium). The membrane has to be molded in the three-dimensional form of the augmented ridge and the adjacent implants or teeth. This time consuming process is carried out by trial and error during the operation. Another fact that makes working with the GBR membrane even more difficult is that most of the absorbable membranes, when become wet, turn out to be softer, less stable, and more difficult for manipulation. In certain cases the membrane has to be fixated to the surrounding bone by mean of miniature pins or screws to avoid graft mobility and leakage. Again, the exposure time of the grafted area and the membrane during these trials affect the total operation time, and increase the chances of post operative infection as well as other complications.

Several methods and implants using bone grafting techniques are known in the art, for example U.S. Pat. No. 6,722,884 discloses a method for preserving the alveolar ridge surrounding a presently extracted root socket by backfilling the socket with bone grafting material and installing an implant in the root socket area. As described in this publication, the dental implant may be installed apically into the root socket immediately following root extraction. The open area of the root socket surrounding the implant is then backfilled with bone grafting material immediately after the implant placement. In the alternative, the presently extracted root socket is filled with bone grafting material, the bone-growth is promoted in the root socket by the bone grafting material for 2-12 months. Then, after sufficient bone growth has been promoted, an implant is installed in the extraction site area in the normal manner.

Another publication that relates to bone grafting technique is US 20060008773 which describes a titanium-mesh umbrella for bone grafting used to combine with conventional implant and to hold bone grafting material in proper position during dental implant placement procedure. The titanium-mesh umbrella forms a projecting umbrella surface with a curvature in perpendicular direction. After the titanium metal umbrella has been positioned a guide tissue membrane can than be securely attached and a space for bone growth can be maintained.

However, there is still a need for an implant and a procedure for using it that is less time consuming and consequently would reduce the costs associated therewith would lower the complications rate.

SUMMARY OF THE INVENTION

It is object of the present invention to provide a dental implant and methods for its use, for performing a safer and less time consuming dental implantation procedure in areas require bone grafting.

It is another object of the present invention to provide methods and a dental implant to enable injecting grafting material in a clean and sterile way from a sealed container to the designated grafting space without exposing the grafting material to oral contamination.

It is yet another object of the present invention to provide a dental implant and methods, for simplifying the placement of biological barrier, a step which is a rather complicated step in existing GBR procedures, which in turn minimize the exposure of the membrane to contaminations.

It is still another object of the invention to provide a novel implant for reconstruction the dentition in areas of sub-optimal edentulous ridge which will enable improving conventional procedures.

It is another object of the present invention to provide a dental implant that comprises all components required in the process in one sterilized package.

Other objects of the invention will become apparent as the description of the invention proceeds.

According to a first embodiment of the present invention there is provided a dental implant for coupling an artificial tooth to a jawbone of a patient which comprises an elongated body having a first (apical) end threaded bone-engaging portion for engaging the dental implant with said jawbone and is preferably designed to provide initial mechanical stability and a second (coronal) end that serves as a post or prothetic platform, preferably made of Titanium, and wherein the dental implant is adapted to enable introducing bone grafting material into a grafting space extending between the elongated body of the dental implant and the patient's jawbone surrounding it.

In accordance with an embodiment of the invention, the dental implant comprises one or more longitudinal grooves located at the external surface of the threaded bone-engaging portion of the dental implant.

This arrangement is particularly advantageous in cases where the quantity or the quality of the available bone at the implantation site is less than satisfactory. In such cases, while inserting the threaded bone-engaging portion of the dental implant into the patient's jawbone, bone particles are accumulated within the one or more longitudinal grooves, and while the insertion of the dental implant continues inwardly (inside the patient's jawbone), the one or more longitudinal grooves are adapted to enable delivering the autogenic bone particles extracted from the perimeter of a drilled hole in a patient's jawbone during insertion of the dental implant in a coronal direction to the grafting space. The coronal extension of the grooves may deliver the grafting material from the container to the grafting space in an apical direction.

According to another embodiment of the invention, the one or more longitudinal grooves extend substantially from the first (apical) end of the dental implant to the second (coronal) end thereof.

By still another embodiment of the invention, the elongated body of the dental implant comprises circumferentially located openings to allow discharge of the bone grafting material into a grafting space extending between the elongated body of the dental implant and the patient's jawbone surrounding it.

In accordance with yet another embodiment of the invention, the dental implant is adapted to enable conveying the bone grafting material from a container containing the bone grafting material towards the first (apical) end of the dental implant. The container may be detachably connected to the second (coronal) end of the elongated body of the dental implant, or in the alternative be located as a cartridge in a motorized handpiece. According to this embodiment the bone grafting material is delivered depending on the geometry of the elongated body of the dental implant. For example, it may be delivered through the inner space of a hollow elongated body of the dental implant, or externally, e.g. when the elongated body comprises one or more grooves externally extending longitudinal grooves.

According to still another embodiment, the container further comprises a pump system for sterilely delivering the bone grafting material from the container towards the grafting space, at which the bone grafting material is to be discharged.

In accordance with still another embodiment of the invention, the dental implant further comprises a skirt shaped semi-permeable membrane, preferably made of collagen (optionally enforced by using a Titanium wire skeleton) and attached to the elongated body so as to at least partially cover the coronal part of the threaded end, and adapted to be positioned either in a first upwardly raised position or in a second downwardly spread position, wherein the latter position is adapted to provide a cover for the grafting space. Using such a skirt shaped semi-permeable membrane allows introducing the bone grafting material into a substantially closed space confined by the skirt shaped semi-permeable membrane being in its second downwardly spread position, thereby covering the missing jawbone at the grafting space, including the hole drilled in a patient's jawbone into which the elongated body of the dental implant was inserted.

In accordance with another preferred embodiment of the present invention the skirt shaped semi-permeable membrane is made of xenogenic or recombinant humanic collagen.

By another preferred embodiment, the second (coronal) end of the elongated body comprises a holding means adapted to hold a temporary crown or a healing cup after detaching the container of the bone grafting material.

According to still another embodiment, the dental implant further comprises a one-way valve adapted to prevent backward reflux of the discharged grafting material from the site at which the grafting material would be discharged back towards the container.

By yet another embodiment the dental implant further comprises a spacer (e.g. a ring) or other device for connecting the skirt shaped semi-permeable membrane to the elongated body of the dental implant and for maintaining a space between the elongated body and the skirt shaped semi-permeable membrane.

According to another aspect of the present invention there is provided a method for carrying out a dental implantation procedure which comprises the steps of:
  a. drilling a cavity at a site in a patient's jawbone for inserting thereat a first (apical) end of a dental implant. The drilling of the cavity is carried out at the designated site, and the cavity should have proper dimensions to allow safe, yet stable positioning of the dental implant thereat. The drilling is preferably carried out by using an appropriate implant speed-reduced physio-dispenser driven torque-controlled handpiece into the residual ridge to the desired (or available) depth and angle according to the planned prosthodontic restoration;
  b. inserting the dental implant at its intended position and affixing the first (apical) end of the dental implant to a native host bone at that site. This may be done by using a torque-controlled handpiece at a low speed;
  c. filling a grafting space defined by the implant and the surrounding jawbone, with a bone grafting material delivered through the dental implant and/or via longitudinally arranged grooves extending at the outer surface of the dental implant; and
  d. placing a temporary crown on top of the dental implant.

In case that the dental implant is not yet ready for full occlusal load, a healing cup would be placed instead.

In the case that the dental implant comprises longitudinally arranged grooves extending at the outer surface of the dental implant, these grooves may be used both as vents, to enable delivering autogenic bone particles, extracted from the perimeter of the hole being drilled in the jawbone during the dental implant insertion, in a coronal direction to the bone defect grafting space, and/or to deliver the grafting material from the container to the grafting space in an apical direction.

In case the dental implant comprises a skirt shaped semi-permeable membrane as described above, step b is carried out while the skirt shaped semi-permeable membrane is in an upwardly raised position.

By another embodiment of this aspect of the invention, upon inserting the dental implant at its intended position the skirt shaped semi-permeable membrane is positioned in its downwardly position, while taking care that it covers all bone-defect edges, and preferably suturing the flap formed (preferably in a water-tight and tension-free fashion) over the still loose skirt shaped semi-permeable membrane being in its downwardly spread position.

The step of filling a space may comprise inserting a pump shaft adapter for driving a pump to deliver the grafting material from the container through the implant and/or through the longitudinally arranged grooves of the implant into a grafting space defined by the implant and the surrounding jawbone. While the material is pressurized in the grafting space, resistance to the pump operation is progressively built until it reaches a pre-defined level set by means of maximum revolving torque of the headpiece. One of the major advantages associated with this embodiment is that it minimizes overfilling the grafting space.

By still another embodiment, the bone grafting material is discharged from a container containing the bone grafting material that is detachably connected to the dental implant.

According to another embodiment of the present invention drilling, affixing of the dental implant (e.g. by screwing it to the native host bone) and motorizing of the pump main shaft is carried out by using a low speed dental handpiece provided with torque control. The reason, being to avoid over-drilling, over screwing and over filling in proximity to the alveolar nerve and to the maxillary sinus.

In accordance to another embodiment of the present invention, the grafting material which is use for bone regeneration (GBR) using Polypeptide growth factors and/or autogenic or xenogenic or allogenic bone graft and/or allopllastic bone-substitute grafting material) and a biological barrier (membrane), may either be prepared and sterilely packed as a part of the product, or be prepared before the implantation procedure starts, and stored in the container which is comprised in the dental implant.

According to another embodiment of the present invention, the bone grafting material is injected by using a novel "pressure casting" technique.

BRIEF DESCRIPTION OF THE DRAWINGS

For a more complete understanding of the present invention, reference is made to the following detailed description taken in conjunction with the accompanying drawing wherein.

DETAILED DESCRIPTION OF PREFERRED EMBODIMENTS

For a more complete understanding of the present invention, reference is made to the following detailed description taken in conjunction with the accompanying drawings.

Let us first consider a case where an artificial tooth should be implanted where the jawbone has a defect and therefore the procedure must include bone grafting stage as well.

Figure 1:
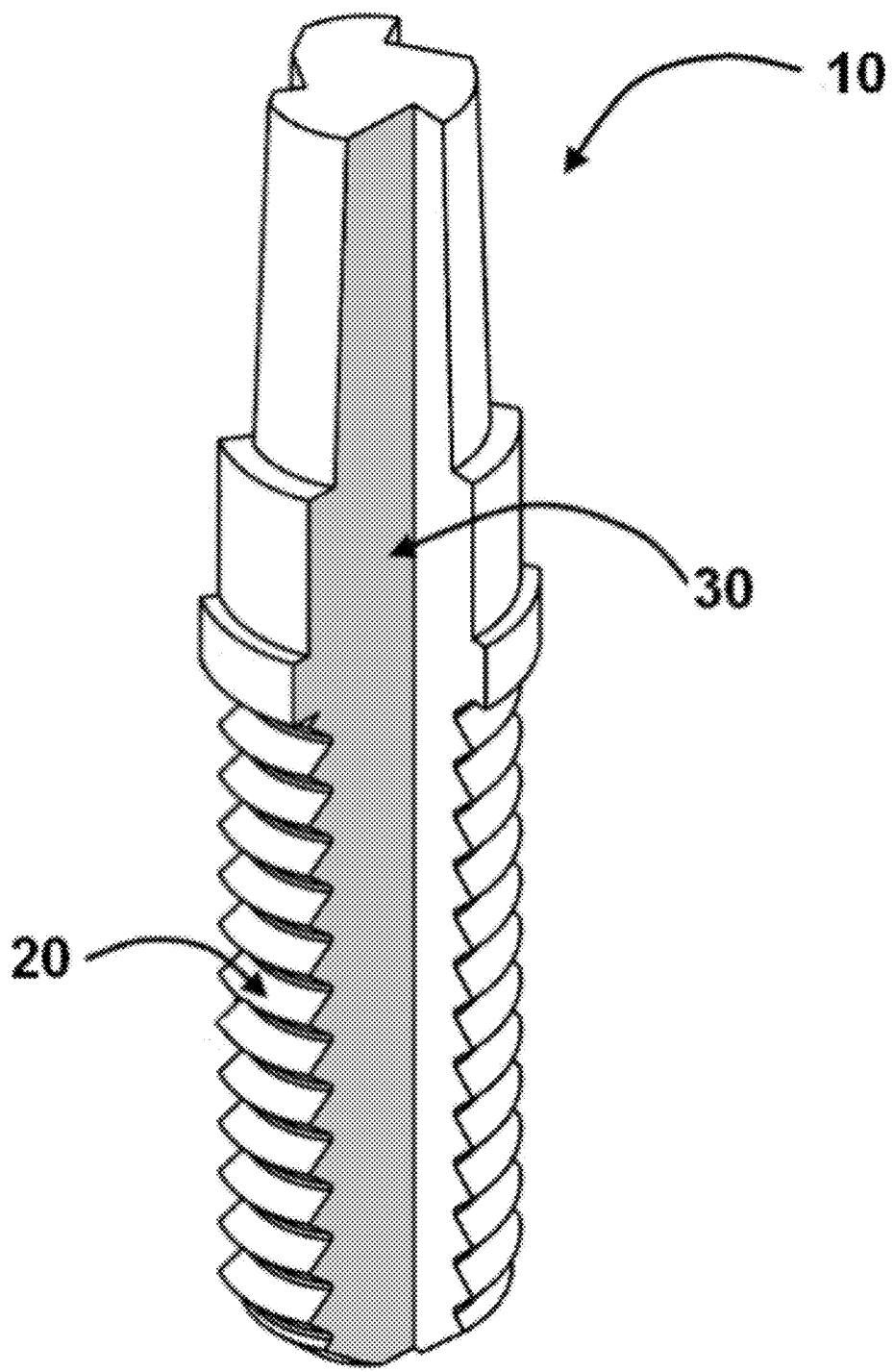
FIG. 1—presents a schematic view of a dental implant according to one embodiment of the present invention.

FIG. 1 presents a schematic view of a dental implant (10) construed in accordance with another embodiment of the present invention. In this example, dental implant 10 comprises an thread type elongated body (20) adapted to engage the edentulous alveolar ridge bone of the patient and three longitudinal grooves (30) arranged at essentially the same circumferential distances from each other. The grooves may used as conduits to enable extracting autogenic bone particles from the perimeter of the hole being drilled in the jawbone during the dental implant insertion, in a coronal direction to the bone defect grafting area. At the same time these grooves may be used as conduits through which the bone grafting material is conveyed to the implant site, after positioning the skirt at its final position. Thus, a couple of the main advantages that may be achieved by using this dental implant are:
(i) its ability to cut the bone (whenever necessary) during its insertion to the jawbone, while removing (upwardly) the jawbone particles being accumulated at the implantation site during this procedure; and
(ii) its ability to convey the bone grafting material via the longitudinal grooves towards the implantation site.

Figure 2:
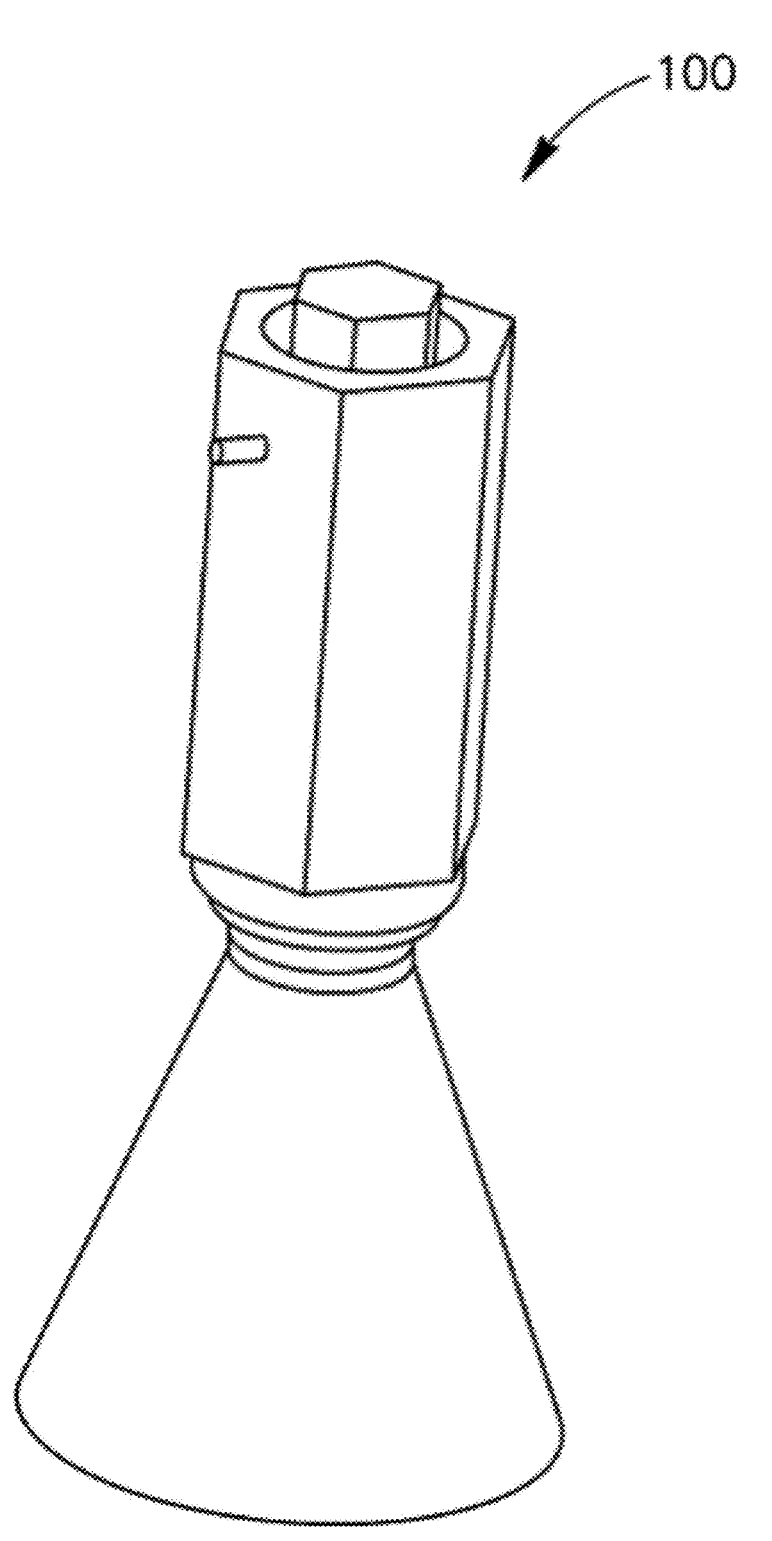
FIG. 2—presents a schematic view of a dental implant according to another embodiment of the present invention.
Figure 3:
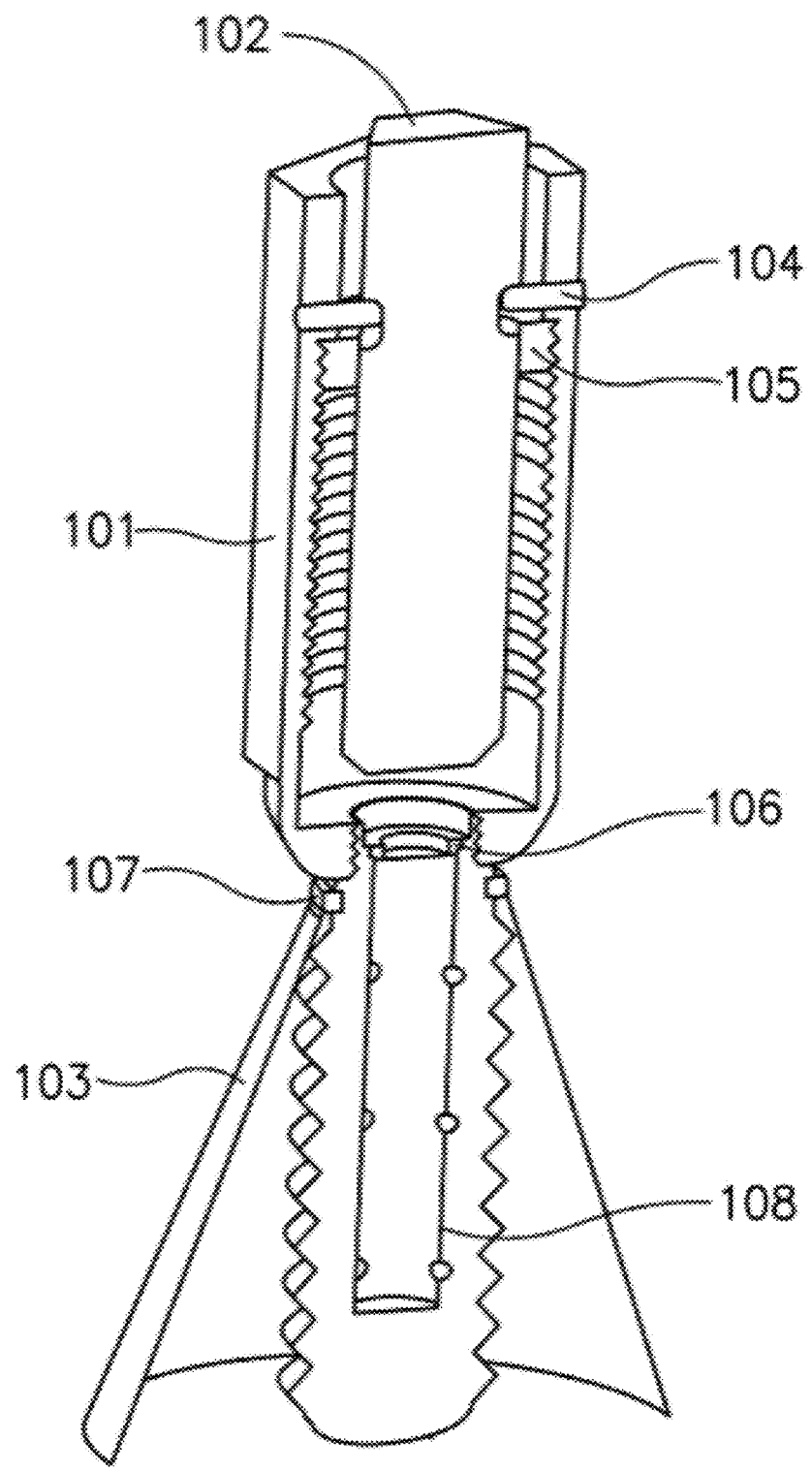
FIG. 3—presents a cross section view of the dental implant shown in FIG. 2.
Figure 4:
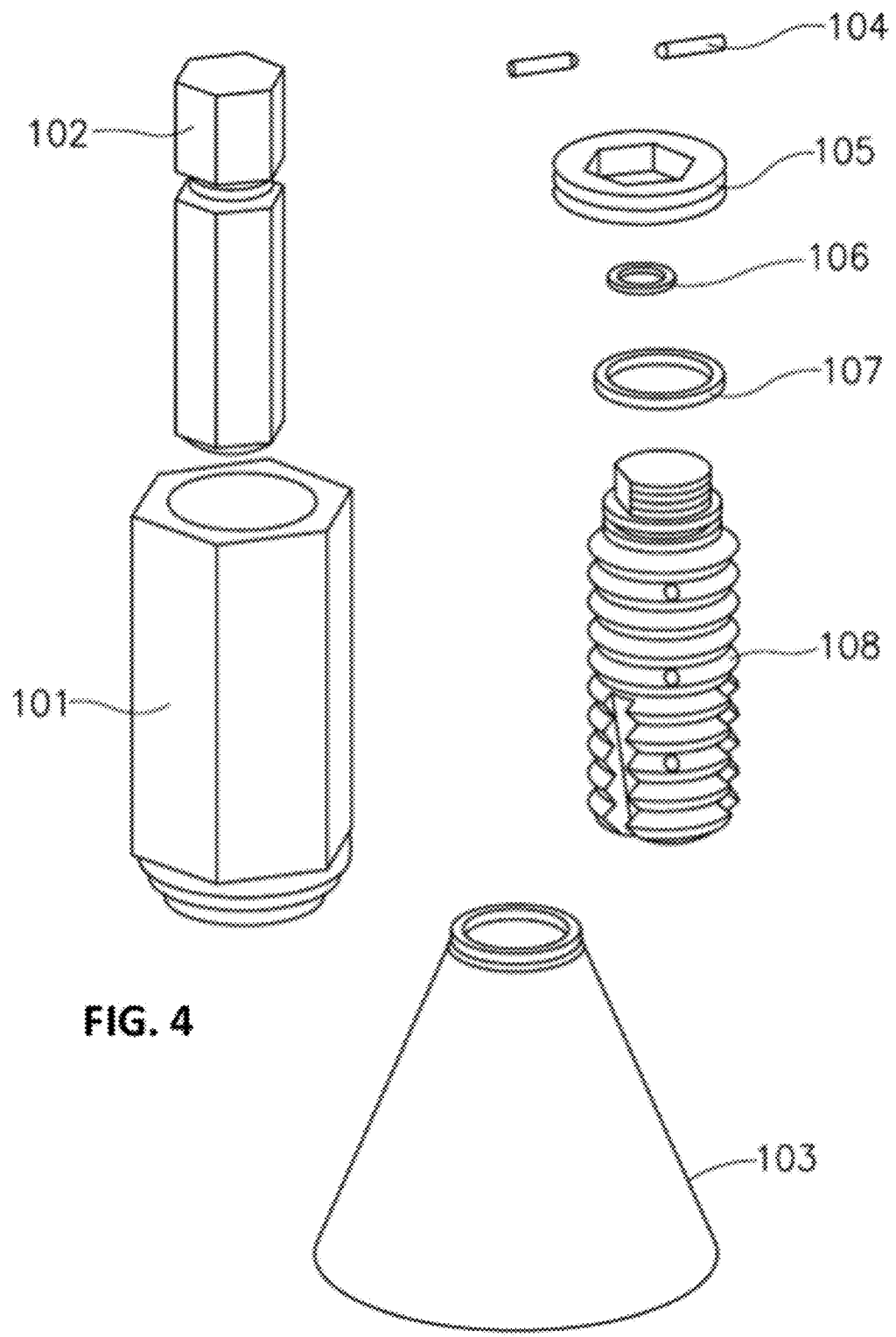
FIG. 4—presents an exploded view of the dental implant shown in FIG. 2.

FIGS. 2 and 3 present non-limiting examples of schematic views of dental implants construed in accordance with certain embodiments of the present invention for the case referred to above. Dental implant (100) of the present invention comprises a container (101) which is preferably designed to fit dental handpiece and can be detached from the rest of the dental implant once the implant is firmly positioned and the bone grafting material has been injected. The container (101), comprises a pumping means to enable the discharge of the bone grafting materials from the container. Once the implant has been affixed to its position, the handpiece is connected to the head of the main shaft 102 that extends outwardly from container 101. Screwing the main shaft with the handpiece, (e.g. a device that is torque controlled, as known in the art per se) causes disk 105, which acts as a piston, to be driven along main shaft 102 to the internal lumen of the implant, thereby pushing the bone grafting material to be outwardly discharged from the container. A skirt shaped semi-permeable membrane (103), preferably made of a connective tissue such as collagen, is attached to the elongated body (the screw-type implant). The skirt membrane 103 may be positioned in at least two distinctive positions, where the plane at the narrow end of the membrane may be viewed as an axis around which the membrane may change its position from a first upwardly raised position to a second downwardly spread position (and vice versa). The raised mode is preferably used as the initial mode wherein the membrane is contracted to minimize the distance between the wide end of the skirt and the dental implant, in order not to block the surgeon's point of view, thereby enabling the surgeon to affix the dental implant to the jawbone at the optimal location and angle. The spread (downward) position is preferably used after the dental implant has been affixed to the jawbone, and is used to provide a cover for a site surrounding the location at which said artificial tooth is to be implanted. Membrane 103 may further serve as a biological barrier to inhibit connective tissue growth and to guide bone regeneration in the space defined between the implant and the alveolar bone defect in the subperiosteal plane. In addition, the membrane may be made of a semi permeable material and may either be absorbable or non absorbable. As will be appreciated by those skilled in the art, although the shape of the membrane has been described herein as a skirt, any other applicable shape such as a bell or others may be used as long as it is able to function in the manner described above.

In the upper part of the container 101 there are two or more affixing pins (104) that stabilize the bearing house of main shaft (102) while being activated by the handpiece. As should be clear to any person skilled in the art, the purpose of these affixing pins in this example is to stabilize the shaft's bearing house so as to ensure that axis around which the shaft rotates does not deviate from its original position. As was mentioned before, disk (105) is connected to the container and by moving along the main shaft it presses the grafting material to the internal lumen of the implant and through number of tunnels spreading the grafting material towards the defect to be augmented. Below the container there might be a one-way-valve (106), designed to prevent backward reflux of the biomaterial from the internal lumen to the container. In addition a spacing ring (107) connects the skirt membrane to the implant and maintains space between the implant and the membrane.

The lower part of the dental implant comprises a screw-type Titanium portion (108) that is adapted to be screwed into the edentulous alveolar ridge bone. The screw-type Titanium portion has an internal lumen and number of tunnels that direct the grafting material from the container through the internal lumen to the augmented bone defect.

Once the space of the augmented bone defect has been filled with the bone grafting material, any further introduction of bone grafting material builds us a pressure in that confined space. Once this pressure (when translated into resistance force) reaches the pre-defined level of the torque control handpiece, the main shaft will not be screwed any further and the handpiece may then be removed.

Figure 5:
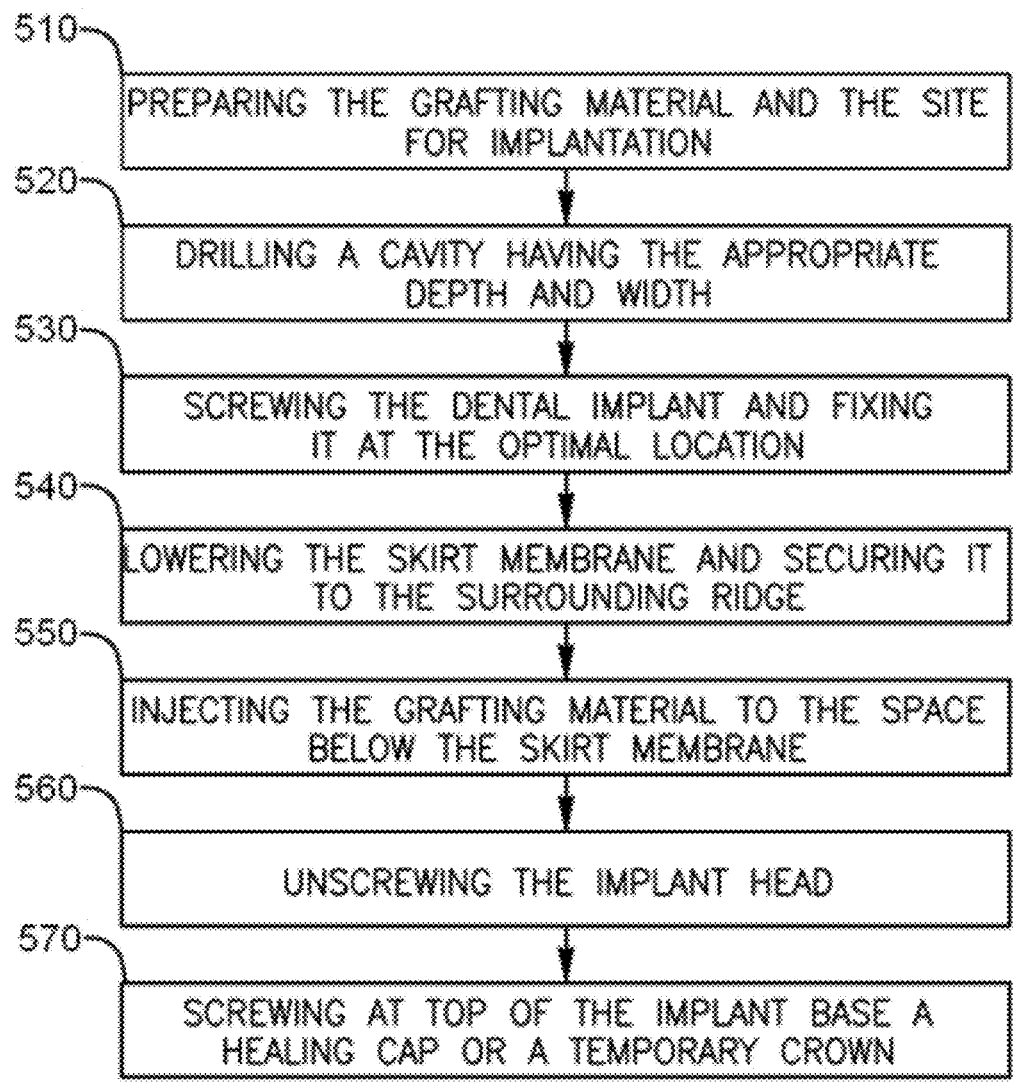
FIG. 5—presents a flow chart of the method provided by the present invention.
Figure 6A:
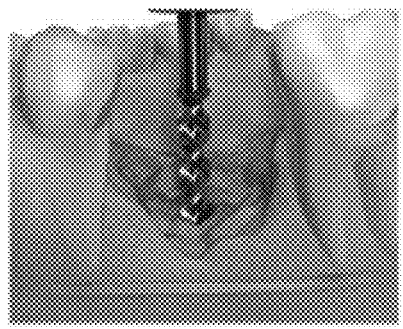
FIGS. 6A to 6E—present steps in the method provided by the present invention.
Figure 6B:
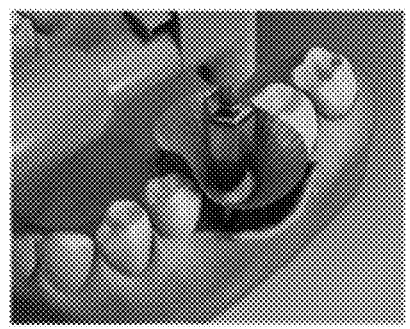
Figure 6C:
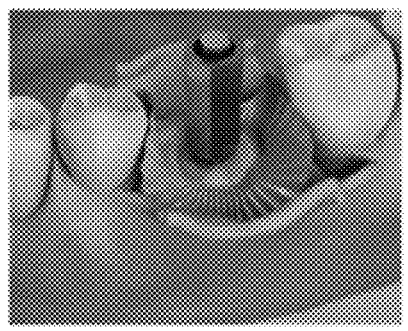
Figure 6D:
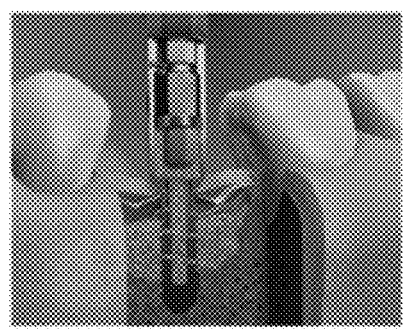
Figure 6E:
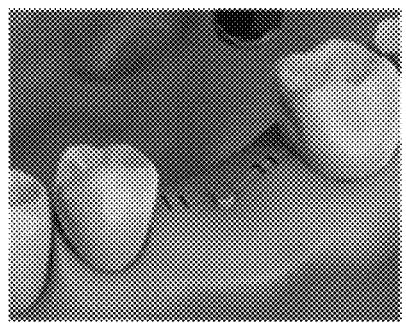

FIG. 5. presents a flow chart describing the steps in the implantation procedure in accordance with an embodiment of the present invention, to enable carrying out the aforementioned stages within only one simpler and shorter session. Similarly, FIGS. 6A to 6E present various stages while carrying out the method provided by the present invention. The first step in FIG. 5 is the preparation step (510) wherein the grafting material is being prepared and filled in the container and the lumen is filled with osteoinductive factors and/or osteoconductive allograft/alloplast grafting materials. The container is then closed and the skirt membrane is confirmed to be in its raised and contracted mode. However, the preferred way of implementing the method provided by the present invention is by using (at the dental clinic) a sealed container provided with the bone grafting material in a ready to use form, rather than to prepare the grafting material under the dental clinic conditions. Another possible alternative could be using a sealed container that comprises the grafting material, and adding saline through a nozzle protruding to that container, to the grafting material.

In step (520), the future site is exposed for grafting and for implant insertion and the granulation tissue is removed. The drilling of a cavity is then carried out with appropriate implant speed-reduced physio-dispenser driven handpiece into the residual ridge to the desired depth, width and angle according to the prosthodontic restoration plan. Following the drilling the implant is screwed (step 530) and located to its optimal location and angle from a prosthodontic point of view, regardless of alveolar ridge form and condition. This step is preferably carried out by using a power-driven handpiece, with speed reduction and torque-control, according to any method known in the art per se. In the embodiment where the dental implant includes the skirt shaped semi-permeable membrane, the insertion of the implant is carried out in this step under direct line of sight as the skirt shaped semi-permeable membrane in its raised position.

Once the implant is affixed to the prepared site, the skirt membrane is lowered from its upwardly raised position into its spread mode (540). During this step, the membrane is flipped around the implant and the surrounding ridge like a tent over a central column followed by suturing the flap over the membrane and circumferentially to the supragingival post. The flap is sutured in a water-tight and tension-free fashion over the still-loose membrane, leaving the implant head ("post") exposed. Upon securing the skirt membrane, the handpiece insertion adapter is replaced with a pump shaft adapter and is employed to drive the pump and deliver the semi-solid grafting material (step 550) from the container through the implant and into the space defined by the implant, the membrane and the surrounding bone. This grafting material may be injected through openings (e.g. tunnels) in the dental implant, in case the bone grafting material is conveyed via an internal space of the dental implant, or the bone grafting material is conveyed via the external longitudinal grooves (if the dental implant comprises such longitudinal grooves) to the surrounding grafting space. Preferably, if the grafting material is injected through the above described openings, the outlet tunnels are angled backward and located at the upper part of the implant threads to avoid bone particles from blocking them during the introduction of the implant. However, after inserting the implant, if there are openings located too close to the implant bottom end, they will anyway be blocked by the jawbone bone to which the implant has been screwed (depending of course of the bone local height at that particular point) and since no bone grafting is required at that point (as the bone is already at that height) they opening will be blocked preventing the bone grafting material from flowing outwardly, and only where the openings are not blocked by the bone, i.e. areas which require augmentation, will be filled by using this mechanism. The one-way-valve prevents the grafting material to reflux backwards, to the container. Among the advantages associated with this type of a procedure one may consider the following:

- Neither membrane design nor fixation to the implant or to the bone is of importance, as the material is discharged underneath the sutured flap.
- Manipulation and delivery of the bone grafting material is done automatically, at accurate amount and in a timely efficient manner.
- At the end of this stage, the grafting material is well condensed around the implant, sealed by the membrane and in direct contact with the grafted bony bed, which is the source for osteoblast cells for guided regeneration.
- The following drawbacks that are associated with prior art methods such as overfilling of bone grafting material, over tension of the flap, exposure of the sterilized bone grafting material, the need for wide flap exposure and release and technically demanding manipulation of the semi solid components, may all be avoided by using the present invention.

Next, the head of the implant (the container and the main shaft) is unscrewed and detached from the implant (560), followed by screwing (570) a healing cup over the post or preparation and cementation of a conventional temporary crown, depending on whether the implant is stable enough to hold the conventional temporary crown.

Therefore, the one-piece implant/post design described in this example offers the following advantages:

i) No microscopic gap is left between the two structures in the biological width adjacent to the crestal peri-implant bone, where such gaps were found to encourage crestal bone resorption around the implant in the long term; and ii) Special anti-rotation mechanisms of internal or external hexagons and screws are currently used by the prior art methods to interconnect the two structures. Unfortunately, structural failure of these mechanisms due to overload is rather common. This in turn might jeopardize the whole long lasting and expensive surgical effort due to premature breakdown of the implant hexagon or shearing the connecting mini-screw inside the implant, despite the fact that the implant is well anchored by means of osseointegration into the alveolar bone. Such mechanisms become redundant for the device of the present invention and the way it is applied.

It is to be understood that the above description only includes some embodiments of the invention and serves for its illustration. Although the present invention has been described with reference to presently preferred embodiments and practices, it should be understood that various changes and modifications may be devised by a person skilled in the art without departing from the scope of the present invention, and are thus encompassed by the present invention. In particularly, although the implant has been described herein and throughout the specification and claims as being a dental implant, it should be understood to encompass also implants for use in other medical fields such as orthopedic, plastic surgery, neurosurgery and the like, mutatis mutandis.

The invention claimed is:

1. A dental implant for coupling an artificial tooth to a jawbone of a patient which comprises an elongated body having a first end threaded bone-engaging portion for engaging the dental implant with said jawbone and a second end, wherein the dental implant is configured to operate as a conduit for bone grafting material, said dental implant comprising one or more longitudinal grooves located at an external surface of said threaded bone-engaging portion of the dental implant which extend from the second end of said dental implant to the first end thereof, to enable the conveying of said bone grafting material along said one or more of the longitudinal grooves towards a grafting space extending between said elongated body and the patient's jawbone surrounding it, wherein said dental implant further comprises a skirt shaped semi-permeable membrane, made of collagen and attached to the elongated body so as to at least partially cover a coronal part of the threaded end, and adapted to be positioned either in a first upwardly raised position or in a second downwardly spread position, wherein the latter position is adapted to provide a cover for the grafting space.

2. The dental implant according to claim 1, wherein said skirt shaped semi-permeable membrane is made of xenogenic or recombinant humanic collagen.

3. A dental implantation procedure which comprises the steps of:
   (i) drilling a cavity at a site in a patient's jawbone for inserting thereat a first end of a dental implant;
   (ii) inserting the dental implant at its intended position;
   (iii) filling a grafting space defined by the implant and the surrounding jawbone, with a bone grafting material delivered through a space extending from a top end of the dental implant and/or via longitudinally arranged grooves extending from the top end of the dental implant at the outer surface thereof;
   (iv) connecting a temporary crown on the top end of the dental implant, and
   wherein said dental implant comprises a skirt shaped semi-permeable membrane made of collagen which covers at least partially the coronal part of a threaded end of said dental implant, and which is configured to be positioned either in a first upwardly raised position or in a second downwardly spread position, wherein the latter position is configured to provide a cover for the grafting space, and wherein step (ii) is carried out while the skirt shaped semi-permeable membrane is in an upwardly raised position.

4. The dental implantation procedure according to claim 3, wherein upon inserting the dental implant at its intended position the skirt shaped semi-permeable membrane is positioned in its downwardly position, while taking care that it covers all bone-defect edges.

* * * * *